US012653801B2

(12) United States Patent
Iitsuka et al.

(10) Patent No.: US 12,653,801 B2
(45) Date of Patent: Jun. 16, 2026

(54) DIGESTIVE LIPASE ACTIVITY INHIBITOR, BLOOD TRIGLYCERIDE CONCENTRATION INCREASE INHIBITOR, AND FAT ABSORPTION INHIBITOR

(71) Applicants: Pharma Foods International Co., Ltd., Kyoto (JP); Mitsui DM Sugar Co., Ltd., Tokyo (JP)

(72) Inventors: Hiroaki Iitsuka, Kyoto (JP); Sayo Morita, Kyoto (JP); Keita Koga, Kyoto (JP); Atsushi Yamatsu, Kyoto (JP); Mujo Kim, Kyoto (JP); Toma Furuta, Tokyo (JP)

(73) Assignees: Pharma Foods International Co., Ltd., Kyoto (JP); Mitsuj DM Sugar Co., Ltd, Tokyo (JP)

( * ) Notice: Subject to any disclaimer, the term of this patent is extended or adjusted under 35 U.S.C. 154(b) by 516 days.

(21) Appl. No.: 18/018,951

(22) PCT Filed: Aug. 2, 2021

(86) PCT No.: PCT/JP2021/028604
§ 371 (c)(1),
(2) Date: Jan. 31, 2023

(87) PCT Pub. No.: WO2022/030442
PCT Pub. Date: Feb. 10, 2022

(65) Prior Publication Data

US 2023/0277493 A1 Sep. 7, 2023

(30) Foreign Application Priority Data

Aug. 3, 2020 (JP) ................................ 2020-131574

(51) Int. Cl.

| | |
|---|---|
| ***A61K 31/201*** | (2006.01) |
| ***A23L 33/12*** | (2016.01) |
| ***A61P 3/04*** | (2006.01) |
| ***A61P 3/06*** | (2006.01) |

(52) U.S. Cl.
CPC ............ *A61K 31/201* (2013.01); *A23L 33/12* (2016.08); *A61P 3/04* (2018.01); *A61P 3/06* (2018.01)

(58) Field of Classification Search
CPC ............. A61K 31/201; A61P 3/04; A61P 3/06
See application file for complete search history.

(56) References Cited

FOREIGN PATENT DOCUMENTS

| | | | | |
|---|---|---|---|---|
| CN | 101579020 A | 11/2009 | | |
| CN | 103284151 A | 9/2013 | | |
| CN | 104814948 A | 8/2015 | | |
| JP | 2005-289951 A | 10/2005 | | |
| JP | 2006-169181 A | 6/2006 | | |
| JP | 2010-209051 A | 9/2010 | | |
| JP | 2014-079207 A | 5/2014 | | |
| JP | 2014-172901 A | 9/2014 | | |
| WO | WO-2009043879 A1 * | 4/2009 | ................ | A61P 9/00 |
| WO | 2017/141879 A1 | 8/2017 | | |

OTHER PUBLICATIONS

Nakagome et al., "Search for pancreatic lipase inhibitory components in Southeast Asian plants", Proceedings of the 2013 Annual Meeting of the Japan Society for Bioscience and Biotechnology (2013) (see partial English translation).
Hongo et al., "Standard Physiology," Igaku-Shoin Ltd., p. 698, 699, 738-741 (2005) (see partial English translation).
Tanaka et al., "New Pharmacology", Nankodo Co Ltd., 402-403 (1997) (see partial English translation).
Marrelli et al., "Metabolite profiling and biological properties of aerial parts from *Leopoldia comosa* (L.) Parl.: Antioxidant and anti-obesity potential," South African Journal of Botany, 120: 104-111 (2018).
Kwasowski et al., "Effects of fatty acid chain length and saturation on gastric inhibitory polypeptide release in obese hyperglycaemic (ob/ob) mice," Bioscience Reports, 5: 701-705 (1985).
Yamada, "3. Extra-pancreatic effects of incretin," Journal of the Japan Diabetes Society, 52 (6): 423-425 (2009) (see partial English translation).
Kurihara et al., "A visceral fat reduction effect of enoki mushroom extract", Pharmacometrics, 78, No. 5/6, p. 129 (2010) (see partial English translation).
International Search Report issued in corresponding International Patent Application No. PCT/JP2021/028604 dated Aug. 24, 2021.
International Preliminary Report on Patentability and Written Opinion issued in corresponding International Patent Application No. PCT/JP2021/028604 dated Feb. 16, 2023.
Larsson et al., "Effect of phosphatidylcholine and free fatty acids on the activity of pancreatic lipase-colipase," Biochimica et Biophysica Acta, 876: 543-550 (1986).
Wang Jibao, Li Min, Jiang Yongpei, "Clinical Practical Drug Compendium", Shaanxi Science and Technology Press, Mar. 1993, p. 293.
Biao Haiping, Zuo Qun, "Sports Nutrition", Beijing Sport University Press, Mar. 2007, p. 35-p. 37.
Li et al., "Free Linoleic Acid and Oleic Acid Reduce Fat Digestion and Absorption In Vivo as Potent Pancreatic Lipase Inhibitors Derived from Sesame Meal," Molecules, 27: 4910 (2022).

* cited by examiner

*Primary Examiner* — Kevin E Weddington
(74) *Attorney, Agent, or Firm* — Morgan, Lewis & Bockius LLP

(57) ABSTRACT

The present invention relates to a digestive lipase activity inhibitor containing, as an active ingredient, at least one selected from the group consisting of linoleic acid and oleic acid.

12 Claims, 3 Drawing Sheets

DIGESTIVE LIPASE ACTIVITY INHIBITOR, BLOOD TRIGLYCERIDE CONCENTRATION INCREASE INHIBITOR, AND FAT ABSORPTION INHIBITOR

TECHNICAL FIELD

The present invention relates to a digestive lipase activity inhibitor, a blood triglyceride concentration increase inhibitor, and a fat absorption inhibitor. The present invention also relates to a food composition or a pharmaceutical product for inhibiting digestive lipase activity, a food composition or a pharmaceutical product for inhibiting an increase in blood triglyceride concentration, and a food composition or a pharmaceutical product for inhibiting fat absorption.

BACKGROUND ART

The number of obese people is increasing all over the world due to changes in eating habits and lifestyle habits, and the like. Obesity is a risk factor that increases various health risks such as diabetes, hypertension, and cancer, and it is said that 4 million people worldwide die of diseases caused by obesity every year.

Among anti-obesity drugs currently in use, (1) those that act on the appetite center and inhibit appetite (mazindol and the like), (2) those that inhibit fat absorption by inhibiting intestinal lipase (orlistat and the like), and the like are known. Many of these anti-obesity drugs have some kind of side effects, their safety has not yet been established, and thus few of them can be used for long periods of time.

Under such circumstances, as a lipase-inhibiting fat absorption inhibitor in the above (2), obtaining a safer fat absorption inhibitor using a food material is being studied. As food materials having lipase inhibitory activity, *Eucommia ulmoides* (Patent Literature 1); *Pulsatilla chinensis, Buddleja officinalis, Kalopanax pictus, Thuja orientalis*, and *Benincasa* seed (Patent Literature 2); black ginger, red ginger, *Cinnamomum sieboldii*, barley grass, black garlic, *Uncaria gambir, Hydrangea macrophylla*, myrobalan, pomegranate, linseed, sweet osmanthus, *Sarcandra glabra*, rockfoil, jasmine tea, oregano, olive leaf, seaberry, and curry leaf (Patent Literature 3); and *Psychotria serpens* (Patent Literature 4) are known.

CITATION LIST

Patent Literature

[Patent Literature 1] Japanese Unexamined Patent Publication No. 2005-289951

[Patent Literature 2] Japanese Unexamined Patent Publication No. 2006-169181

[Patent Literature 3] Japanese Unexamined Patent Publication No. 2010-209051

[Patent Literature 4] Japanese Unexamined Patent Publication No. 2014-172901

SUMMARY OF INVENTION

Technical Problem

However, many of the above-mentioned food materials are not widely distributed in the market, which may lead to high costs and low supply. Furthermore, when a sufficient amount of active ingredients contained in food materials is ingested, the intake of the food materials themselves increases proportionally. Therefore, elucidation and utilization of active ingredients that are easy to ingest more efficiently are required. Therefore, from the viewpoints of availability, cost reduction, ingestion efficiency, and the like, there is a demand for agents useful for fat absorption inhibition and the like using more familiar food-derived active ingredients.

One aspect of the present invention has been made based on the above circumstances, and the object thereof is to provide a novel digestive lipase activity inhibitor, blood triglyceride concentration increase inhibitor, and fat absorption inhibitor.

Solution to Problem

The present inventors have found that linoleic acid or oleic acid and mixtures thereof have an action of inhibiting digestive lipase activity and an action of inhibiting an increase in blood triglyceride concentration, and that these effects are more pronounced when linoleic acid and oleic acid are used in combination. Accordingly, the present inventors found that these components have an effect as a fat absorption inhibitor, and completed the present invention.

In other words, according to an aspect of the present invention, there is provided a digestive lipase activity inhibitor comprising, as an active ingredient, at least one selected from the group consisting of linoleic acid and oleic acid.

According to another aspect of the present invention, there is provided a blood triglyceride concentration increase inhibitor comprising, as an active ingredient, at least one selected from the group consisting of linoleic acid and oleic acid.

According to still another aspect of the present invention, there is provided a fat absorption inhibitor comprising, as an active ingredient, at least one selected from the group consisting of linoleic acid and oleic acid.

According to still another aspect of the present invention, there is provided a food composition for inhibiting digestive lipase activity or a pharmaceutical product for inhibiting digestive lipase activity, comprising, as an active ingredient, at least one selected from the group consisting of linoleic acid and oleic acid.

According to still another aspect of the present invention, there is provided a food composition for inhibiting an increase in blood triglyceride concentration or a pharmaceutical product for inhibiting an increase in blood triglyceride concentration, comprising, as an active ingredient, at least one selected from the group consisting of linoleic acid and oleic acid.

According to still another aspect of the present invention, there is provided a food composition for inhibiting fat absorption or a pharmaceutical product for inhibiting fat absorption comprising g, as an active ingredient, at least one selected from the group consisting of linoleic acid and oleic acid.

The above agents, food compositions, or pharmaceutical products may comprise both linoleic acid and oleic acid as active ingredients.

Advantageous Effects of Invention

According to the present invention, it is possible to provide a novel digestive lipase activity inhibitor, blood triglyceride concentration increase inhibitor, and fat absorption inhibitor. In addition, according to the present invention, a novel food composition or pharmaceutical product for inhibiting digestive lipase activity, a novel food composition or pharmaceutical product for inhibiting an increase in blood triglyceride concentration, and a novel food composition or pharmaceutical product for inhibiting fat absorption can also be provided.

DESCRIPTION OF EMBODIMENTS

Figure 1:
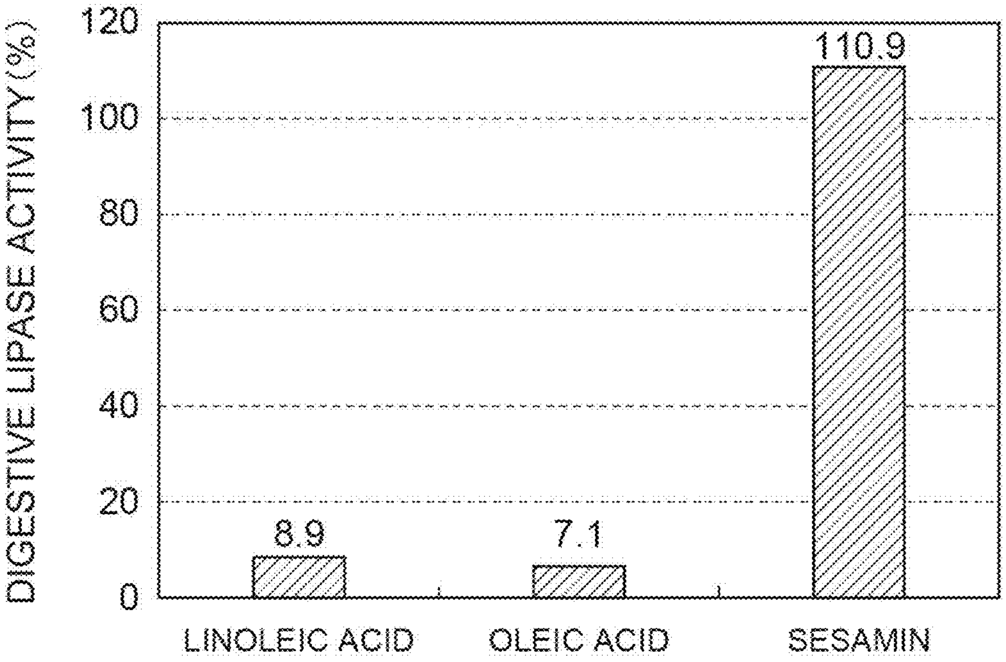
FIG. 1 is a graph showing a digestive lipase activity inhibitory effect of linoleic acid and oleic acid.

Embodiments of the present invention will be described below, but the present invention is not limited to the following embodiments.

One embodiment of the present invention provides a digestive lipase activity inhibitor containing, as an active ingredient, at least one selected from the group consisting of linoleic acid and oleic acid. In order to obtain the digestive lipase activity inhibitory effect more effectively, the digestive lipase activity inhibitor may contain both linoleic acid and oleic acid as active ingredients.

In the present specification, the term "digestive lipase" refers to a lipase that is secreted from organs involved in digestion such as the stomach, intestines (including the duodenum, small intestine, and large intestine), and pancreas and acts in the digestive tract, and more specific examples thereof include gastric lipase secreted from the stomach, intestinal lipase secreted from the duodenum, small intestine, or large intestine, and pancreatic lipase secreted from the pancreas. Intestinal lipase and pancreatic lipase, which mainly act in the intestine, are collectively referred to as "intestinal lipase." Digestive lipase does not include lipases that act in organs other than the digestive tract, such as cardiomyocyte lipoprotein lipase, adipocyte lipase, and the like. A digestive lipase activity inhibitor is an agent that inhibits the activity of these digestive lipases.

In the present specification, linoleic acid includes a compound represented by the following formula (1), isomers of the compound, and derivatives of the compound represented by the following formula (1) (linoleic acid derivatives). The linoleic acid is preferably a compound represented by the following formula (1) from the viewpoint of making it easier to obtain the inhibitory action on the digestive lipase activity. Examples of isomers of linoleic acid include conjugated linoleic acid and non-conjugated linoleic acid. Non-conjugated linol is preferable from the viewpoint of making it easier to obtain the inhibitory action on the digestive lipase activity. Examples of linoleic acid derivatives include oxides of linoleic acid. From the viewpoint of making it easier to obtain the inhibitory action on the digestive lipase activity, the linoleic acid derivative is preferably a derivative other than the oxide of linoleic acid.

(1)

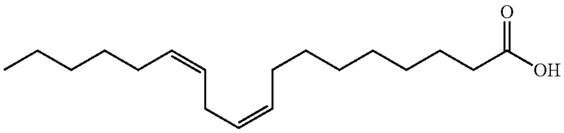

In the present specification, oleic acid includes a compound represented by the following formula (2), isomers of the compound, and derivatives of the compound represented by the following formula (2) (oleic acid derivatives). The oleic acid is preferably a compound represented by the following formula (2) from the viewpoint of making it easier to obtain the inhibitory action on the digestive lipase activity. Isomers of oleic acid include elaidic acid and the like. Examples of derivatives of oleic acid include methyl oleate and the like.

(2)

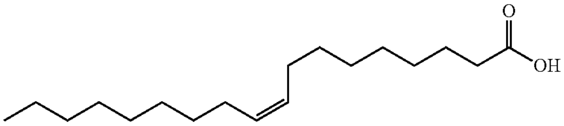

Linoleic acid and oleic acid may be chemically synthesized or may be obtained from foods such as sesame and soybeans. In the specification, linoleic acid and oleic acid refer to free linoleic acid and free oleic acid, excluding linoleic acid and oleic acid as constituents of triglycerides.

The content of the active ingredient in the digestive lipase activity inhibitor may be appropriately set depending on the form of the digestive lipase activity inhibitor, the purpose of use, and the like, but may be, for example, 0.0001% by mass or more, 0.001% by mass or more, 0.01% by mass or more, 0.1% by mass or more, or 1% by mass or more, and may be 100% by mass or less, 50% by mass or less, or 5% by mass or less, based on total amount of digestive lipase activity inhibitor.

The digestive lipase activity inhibitor according to the present embodiment may contain only the above active ingredients, or may further contain other ingredients as long as the effects of the present invention are not hindered. Other ingredients may be materials that can be used for food compositions, quasi-drugs, or pharmaceutical products. Materials that can be used for food compositions, quasi-drugs, or pharmaceutical products are not particularly limited, and examples thereof include amino acids, proteins, carbohydrates, fats and oils, sweeteners, minerals, vitamins, flavoring agents, excipients, and binders, lubricants, disintegrators, emulsifiers, surfactants, bases, solubilizers, and suspending agents.

Examples of proteins include milk casein, whey, soybean protein, wheat protein, and egg white. Examples of carbohydrates include corn starch, cellulose, pregelatinized starch, wheat starch, rice starch, and potato starch. Examples of fats and oils include salad oil, corn oil, soybean oil, safflower oil, olive oil, and palm oil. Examples of sweeteners include saccharides such as glucose, sucrose, fructose, glucose-fructose syrup, and fructose-glucose syrup; sugar alcohols such as xylitol, erythritol, and maltitol; artificial sweeteners such as sucralose, aspartame, saccharin, and acesulfame K; and *stevia* sweeteners. Examples of minerals include calcium, potassium, phosphorus, sodium, manganese, iron, zinc, and magnesium; and salts thereof. Examples of vitamins include vitamin E, vitamin C, vitamin A, vitamin D, B vitamins, biotin, and niacin. Examples of excipients include dextrin, starch, lactose, and crystalline cellulose. Examples of binders include polyvinyl alcohol, gelatin, hydroxypropylmethylcellulose, hydroxypropylcellulose, sodium carboxymethylcellulose, and polyvinylpyrrolidone. Examples of lubricants include magnesium stearate, calcium stearate, and talc. Examples of disintegrators include crystalline cellulose, agar, gelatin, calcium carbonate, sodium hydrogen carbonate, and dextrin. Examples of emulsifiers or surfactants include sucrose fatty acid esters, citric acid, lactic acid, glycerin fatty acid esters, polyglycerin fatty acid esters, sorbitan fatty acid esters, propylene glycol fatty acid esters, and lecithin. Examples of bases include cetostearyl alcohol, lanolin, and polyethylene glycol. Examples of solubilizers include polyethylene glycol, propylene glycol, sodium carbonate, and sodium citrate. Examples of suspending agents include glyceryl monostearate, polyvinyl alcohol, polyvinylpyrrolidone, methylcellulose, hydroxymethylcellulose, and sodium alginate. These may be used alone, or two or more thereof can be used in combination.

The shape of the digestive lipase activity inhibitor according to the present embodiment is not limited, may be in any shape such as solid (powder, granules, and the like), liquid (solution, suspension, and the like), and paste, and may be in any dosage form such as powder, pill, granule, tablet, capsule, troche, liquid, and suspension.

The subject of administration of the digestive lipase activity inhibitor may be a human or an animal, preferably a human. The digestive lipase activity inhibitor may be used for obese patients, diabetic patients, hypertensive patients, and the like, and may be used for healthy people without health problems such as obesity.

The digestive lipase activity inhibitor may be administered orally or may be administered parenterally such as intravenous administration. The digestive lipase activity inhibitor is preferably administered orally.

When the digestive lipase activity inhibitor is orally administered, the active ingredient is preferably administered in an amount of 50 μg or more per dose, more preferably 200 μg or more, and further more preferably 1000 μg or more. In addition, the active ingredient is preferably administered in an amount of 150 μg or more per day, more preferably 600 μg or more, and further more preferably 3000 μg or more. In addition, the active ingredient is preferably administered in an amount of 300 mg or less per dose, more preferably 100 mg or less. In addition, the active ingredient is preferably administered in an amount of 900 mg or less per day, more preferably 300 mg or less. Within this range, the digestive lipase activity can be sufficiently inhibited.

When the digestive lipase activity inhibitor is parenterally administered, the active ingredient is preferably administered in an amount of 50 μg or more per dose, more preferably 200 μg or more, and further more preferably 1000 μg or more. In addition, the active ingredient is preferably administered in an amount of 150 μg or more per day, more preferably 600 μg or more, and further more preferably 3000 μg or more. In addition, the active ingredient is preferably administered in an amount of 300 mg or less per dose, more preferably 100 mg or less. In addition, the active ingredient is preferably administered in an amount of 900 mg or less per day, more preferably 300 mg or less. Within this range, the digestive lipase activity can be sufficiently inhibited.

Digestive lipase activity inhibitors inhibit the activity of digestive lipases such as gastric lipase, intestinal lipase, and pancreatic lipase, thereby inhibiting increases in blood triglyceride concentrations. That is, it can be said that one embodiment of the present invention provides a blood triglyceride concentration increase inhibitor containing, as an active ingredient, at least one selected from the group consisting of linoleic acid and oleic acid.

In the blood triglyceride concentration increase inhibitor according to one embodiment, specific aspects of the active ingredient and the content, administration subject, and dosage thereof may be the same as those of the digestive lipase activity inhibitor described above. That is, regarding the blood triglyceride concentration increase inhibitor according to one embodiment, in the description related to the digestive lipase activity inhibitor described above, "digestive lipase activity inhibitor" may be read as "blood triglyceride concentration increase inhibitor."

Furthermore, the digestive lipase activity inhibitor or blood triglyceride concentration increase inhibitor according to the present embodiment inhibits digestive lipase activity and inhibits the increase in blood triglyceride concentration, thereby inhibiting fat absorption into the body. That is, it can be said that one embodiment of the present invention provides a fat absorption inhibitor containing, as an active ingredient, at least one selected from the group consisting of linoleic acid and oleic acid.

In the fat absorption inhibitor according to one embodiment, specific aspects of the active ingredient and the content, administration subject, and dosage thereof may be the same as those of the digestive lipase activity inhibitor described above. That is, regarding the fat absorption inhibitor according to one embodiment, in the description related to the digestive lipase activity inhibitor described above, "digestive lipase activity inhibitor" may be read as "fat absorption inhibitor."

The digestive lipase activity inhibitor, blood triglyceride concentration increase inhibitor, and fat absorption inhibitor described above can be used for anti-obesity and diet purposes. In addition, it can be used for improvement of skin quality, improvement of cardiovascular disease, improvement of insulin resistance, prevention of diabetes, prevention of cerebral infarction, prevention of fatty liver, prevention of liver cirrhosis, prevention of hypertension, and deodorant for body odor.

The digestive lipase activity inhibitor, the blood triglyceride concentration increase inhibitor, and the fat absorption inhibitor described above may be food compositions, quasi-drugs, or pharmaceutical products for inhibiting digestive lipase activity, for inhibiting an increase in blood triglyceride concentration, or for inhibiting fat absorption, and may be used as a feed or a feed additive when used for animals. Each of the above agents may be used as one component of each product such as food compositions, quasi-drugs, pharmaceutical products, feeds, or feed additives. That is, according to one embodiment of the present invention, food compositions, quasi-drugs, pharmaceutical products, feeds, or feed additives for inhibiting digestive lipase activity, for inhibiting an increase in blood triglyceride concentration, or for inhibiting fat absorption, containing, as an active ingredient, at least one selected from the group consisting of linoleic acid and oleic acid, are provided.

Food compositions for inhibiting digestive lipase activity, for inhibiting an increase in blood triglyceride concentration, or for inhibiting fat absorption may be health foods, foods with function claims, foods for special dietary uses, dietary supplements, supplements, and foods for specified health uses. Specific examples of food compositions include rice, bread, noodles, dairy products, bean products, confectionery, drinks, oil and fat foods, seasonings, and supplements.

Examples of pharmaceutical products or quasi-drugs for inhibiting digestive lipase activity, for inhibiting an increase in blood triglyceride concentration, or for inhibiting fat absorption include uncoated tablets, sugar-coated tablets, granules, powders, tablets, and capsules (hard capsules, soft capsules), and the like.

Examples of feeds or feed additives for inhibiting digestive lipase activity, for inhibiting an increase in blood triglyceride concentration, or for inhibiting fat absorption include companion animal feeds such as dog food and cat food, livestock feeds, poultry feeds, and farmed seafood feeds. "Feed" includes anything orally ingested by an animal for nutritional purposes. More specifically, when classified in terms of nutrient content, examples of feeds include all of rough feeds, concentrated feeds, mineral feeds, and special feeds, and when classified in terms of official standards, examples of feeds include all of compound feeds, mixed feeds, and single feeds. In addition, when classified in terms of feeding method, examples of feeds include all feeds that are directly fed, feeds that are mixed with other feeds, and feeds that are added to drinking water to supplement nutrients.

The content of the active ingredient in each of the above products may be appropriately set in accordance with each product within the range where a suitable dosage of the active ingredient in the digestive lipase activity inhibitor, the blood triglyceride concentration increase inhibitor, or the fat absorption inhibitor described above can be ingested.

The production method of each of the above products is not particularly limited, and any known method can be used as appropriate. For example, production is possible by adding at least one selected from linoleic acid and oleic acid in a suitable adding amount in these production processes.

The present invention described above can also be regarded as a method for inhibiting digestive lipase activity, including the process of administering a composition containing, as an active ingredient, at least one selected from the group consisting of linoleic acid and oleic acid to a subject in need thereof, a method for inhibiting an increase in blood triglyceride concentration, or a method for inhibiting fat absorption.

The present invention described above can also be regarded as a composition containing, as an active ingredient, at least one selected from the group containing of linoleic acid and oleic acid for use in inhibiting digestive lipase activity, for use in inhibiting an increase in blood triglyceride concentration, or for use in inhibiting fat absorption.

The present invention described above can also be regarded as the use (application) of at least one selected from the group consisting of linoleic acid and oleic acid in the production of a digestive lipase activity inhibitor, a blood triglyceride concentration increase inhibitor, or a fat absorption inhibitor.

EXAMPLES

Hereinafter, the present invention will be described in more detail with reference to Examples and the like. However, the present invention is not limited to the following examples.

<Test 1: Digestive Lipase Activity Inhibition Test with Linoleic Acid and Oleic Acid>

Regarding linoleic acid and oleic acid, the digestive lipase inhibitory activity was evaluated by the following method. As linoleic acid and oleic acid, those manufactured by FUJIFILM Wako Pure Chemical Corporation were used.

(Preparation of Digestive Lipase Solution)

30 mL of 0.1 M citrate buffer solution (pH 6.0) was added to 30 mg of rat intestinal acetone powder (manufactured by SIGMA Corporation), shaken in ice for 1 hour, and centrifuged at 4° C. and 10,000 rpm for 45 minutes, to obtain a digestive lipase solution. The digestive lipase solution is a mixture of pancreatic lipase, intestinal lipase, and the like.

(Activity Evaluation)

In a 1.5 mL capacity tube, 10 μL of DMSO solution of 0.19 mg/mL linoleic acid or 0.16 mg/mL oleic acid (concentration is the final concentration at the time of reaction) or dimethyl sulfoxide (DMSO) solution of 0.044 mg/mL sesamin for comparison, and 237 μL of coloring solution, 9 μL of digestive lipase solution, 4 μL of esterase inhibitor, and 90 μL of water were added and incubated at 30° C. for 5 minutes. After that, 25 μL of the substrate solution was added, and the reaction was carried out at 30° C. for 30 minutes in the dark. After that, 700 μL of a reaction stop solution was added, and the absorbance at 412 nm was measured for this solution. As the coloring solution, the substrate solution, the esterase inhibitor, and the reaction stop solution, those attached to Lipase Kit S (manufactured by SB Bioscience Co., Ltd.) were used.

(Control and Blank Evaluation)

A control was prepared in a new 1.5 mL capacity tube for the purpose of measuring the absorbance of the above samples and reagents themselves. As controls, 10 μL of a DMSO solution of 0.19 mg/mL linoleic acid or 0.16 mg/mL oleic acid or a DMSO solution of 0.044 mg/mL sesamin, 237 μL of the coloring solution, 9 μL of the digestive lipase solution described above, 4 μL of an esterase inhibitor, and 90 μL of water were added and incubated at 30° C. for 35 minutes in the dark. After that, 700 μL of reaction stop solution and 25 μL of substrate solution were added, and the absorbance at 412 nm was measured. In addition, blank a was prepared in the same manner as in the activity evaluation except that only DMSO was added instead of the DMSO solution of each sample, and blank b was prepared in the same manner as the control by adding only DMSO (control blank). Absorbance at 412 nm was also measured for blank a and blank b.

(Calculation)

Digestive lipase activity when each sample was added was calculated by the following equation.

$$\text{Digestive lipase activity (\%)}=100\times(\text{absorbance of each sample}-\text{absorbance of control})/(\text{absorbance of blank } a-\text{absorbance of blank } b)$$

(Results)

FIG. 1 shows the calculation results of the digestive lipase activity when each sample was added. While the digestive lipase activity was 110.9% when sesamin was added, the digestive lipase activity was 8.9% when linoleic acid was added and 7.1% when oleic acid was added. Accordingly, it was found that the addition of linoleic acid or oleic acid decreased the digestive lipase activity.

<Test 2: Digestive Lipase Activity Inhibition Test with Mixture of Linoleic Acid and Oleic Acid>

The digestive lipase activity inhibitory effect of a mixture of linoleic acid and oleic acid was studied by the same manner as in Test 1 above. As the linoleic acid and oleic acid, those mentioned above were used. As samples, a 0.009 mg/mL linoleic acid aqueous solution, a 0.008 mg/mL oleic acid aqueous solution, and a mixture of a 0.009 mg/mL linoleic acid aqueous solution and a 0.008 mg/mL oleic acid aqueous solution were used, respectively (the concentration in each sample is the final concentration at the time of reaction measurement).

(Calculation)

First, the digestive lipase activity inhibition rate of each sample was calculated according to the equation shown below.

Digestive lipase activity inhibition rate (%)=100−{100×(absorbance of each sample−absorbance of control)/(absorbance of blank *a*−absorbance of blank *b*)}

In addition, Colby's equation was also used to evaluate whether the mixtures provided synergistic effects. When the measured value is larger than the theoretical value calculated by the following Colby's equation, it can be determined that there is a synergistic effect.

Colby's equation: theoretical value $E=A+B-(A\times B)/100$

A: Digestive lipase activity inhibition rate of linoleic acid (%)

B: Digestive lipase activity inhibition rate of oleic acid (%)

(Results)

Figure 2:
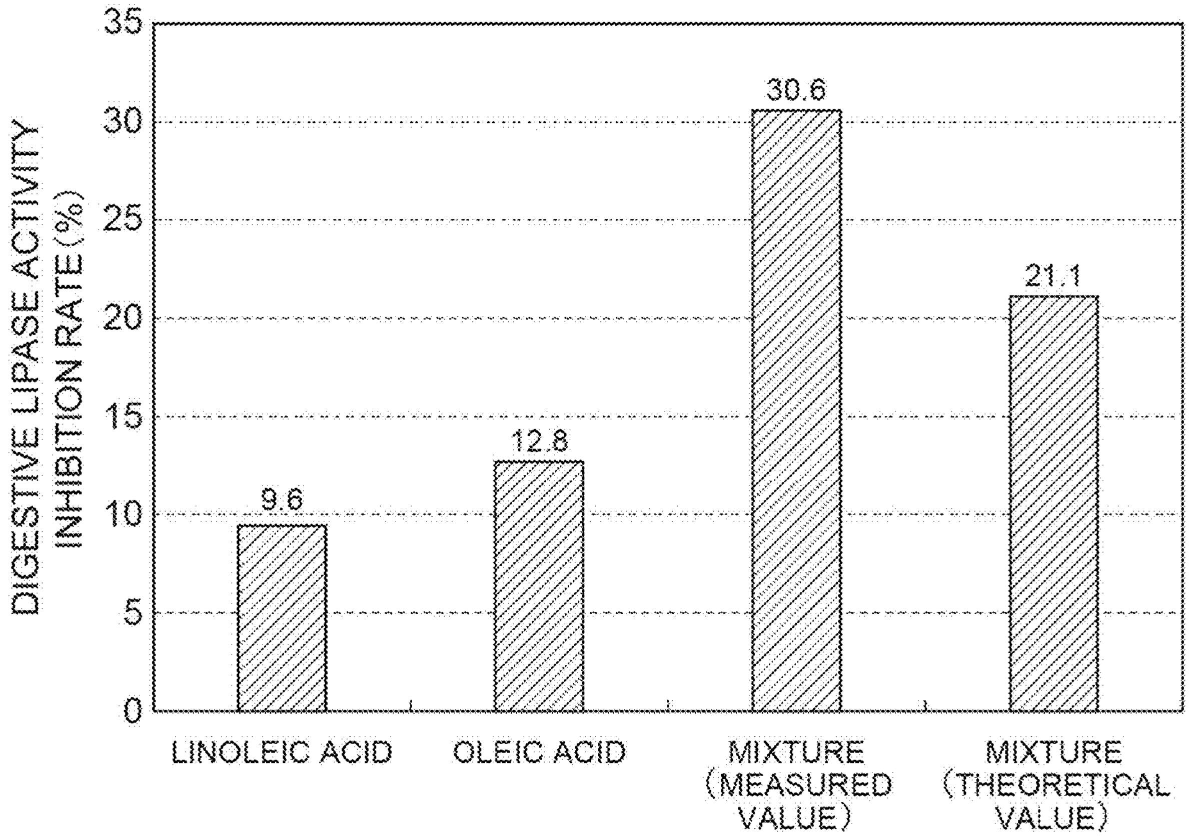
FIG. 2 is a graph showing digestive lipase activity inhibition rates of linoleic acid, oleic acid, and mixtures thereof.

The results are shown in FIG. 2. The digestive lipase activity inhibition rates when linoleic acid, oleic acid, and a mixture thereof were added were 9.6%, 12.8%, and 30.6%, respectively. Since the theoretical value of the digestive lipase activity inhibition rate of the mixture obtained by Colby's equation was 21.1%, it was determined that the mixture of linoleic acid and oleic acid had a synergistic effect of the digestive lipase activity inhibitory action.

<Test 3: Rat Blood Triglyceride Concentration Increase Inhibition Test by Mixture of Linoleic Acid and Oleic Acid>

The following test was used to evaluate whether or not a mixture of linoleic acid and oleic acid has an inhibitory effect on blood triglyceride concentration increase in rats. As the linoleic acid and oleic acid, those mentioned above were used.

(Test Animal)

As rats, Wister Rat (male, 6 weeks old) was used. Rats were bred in a breeding room maintained at an environmental temperature of 23° C., a humidity setting of 55%, and 12 hours of light and darkness (lighting: 8:00 am to 8:00 pm). Tap water was freely ingested as drinking water using an automatic water supply device. The rats were housed individually and acclimatized for 5 days or more after the arrival. Cages and feeders were changed at least once a week.

(Preparation of Lipid-Loaded Diet)

30 mL of corn oil was mixed with 400 mg of cholic acid, 10 g of cholesterol oleate, and 30 mL of pure water were mixed, and the mixture was emulsified by sonicating for 10 minutes to obtain emulsified corn oil for a lipid-loaded diet.

(Test Method)

The rats were weighed and doses were calculated such that 0.46 mg/kg (rat body weight) of linoleic acid and 0.72 mg/kg (rat body weight) of oleic acid could be administered. Linoleic acid and oleic acid were stirred in a 20% (v/v) ethanol solution to prepare a test solution. The rats were divided into two groups, a linoleic acid/oleic acid administration group and a control group (7 rats in each group), and 400 μL of the test solution was orally administered to the linoleic acid/oleic acid administration group. A control group was orally administered with 400 μL of a 20% (v/v) ethanol solution. For all groups, 1 mL of emulsified corn oil, which is a lipid-loaded diet, was orally administered 10 minutes after oral administration. Blood was collected from the rats every 1.5 hours until 7.5 hours after administration of the lipid-loaded diet. After allowing the collected blood to stand for 30 minutes, it was centrifuged (3000 g×15 minutes). Serum was removed after centrifugation and blood triglyceride concentration (mg/dL) was measured. The blood triglyceride concentration was measured according to the measurement method of Lab Assay™ Triglyceride (manufactured by FUJIFILM Wako Pure Chemical Corporation).

(Results)

Figure 3:
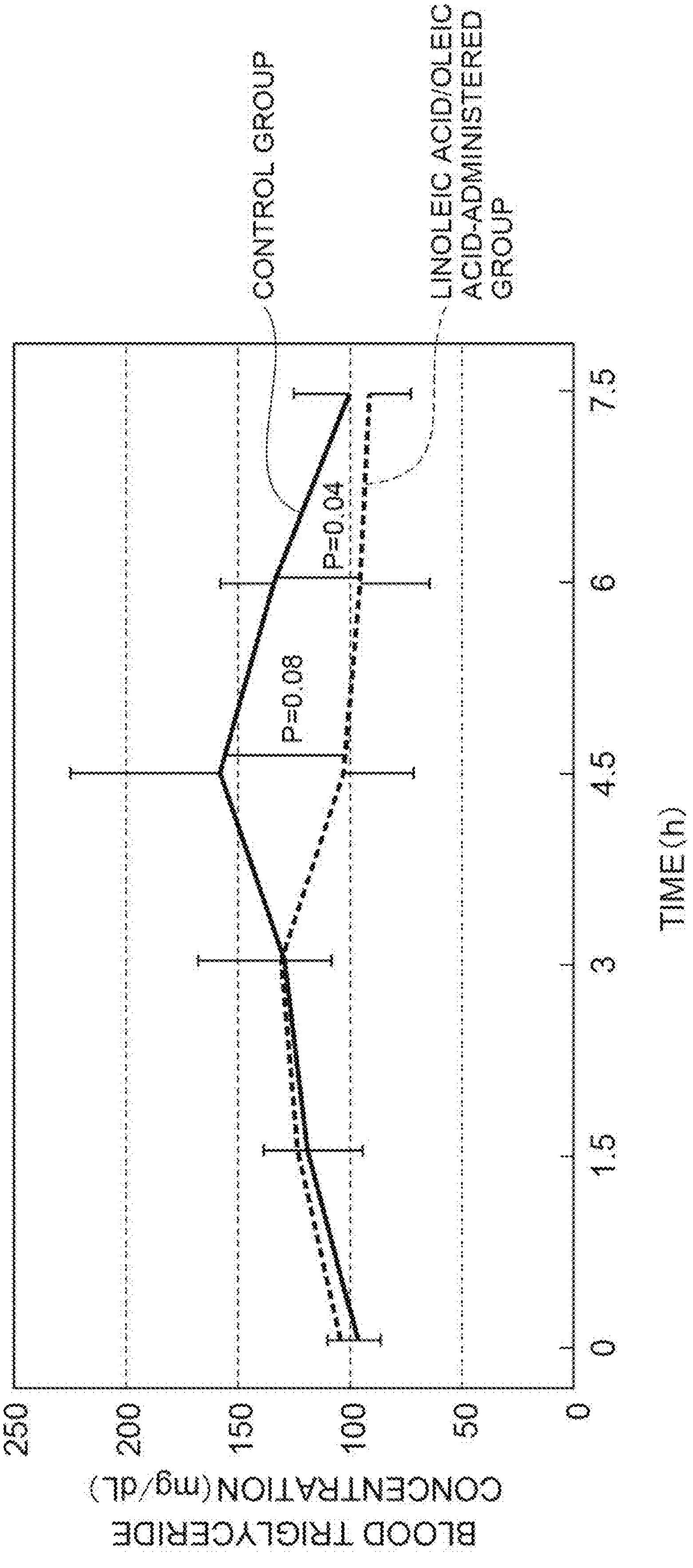
FIG. 3 is a graph showing an inhibitory effect of a mixture of linoleic acid and oleic acid on blood triglyceride concentration increase.

FIG. 3 shows changes in blood triglyceride concentrations in the linoleic acid/oleic acid-administered group and the control group. One of the subjects in the control group became unable to continue the test and was excluded from the control group. Blood triglyceride concentrations in the linoleic acid/oleic acid administration group were significantly lower than those in the control group 6 hours after administration of the lipid-loaded diet (P=0.04), and tended to be inhibited 4.5 hours after administration (P=0.08). Accordingly, it is found that the mixture of linoleic acid and oleic acid inhibits the increase in blood triglyceride concentration. That is, it was confirmed that linoleic acid and oleic acid can inhibit fat absorption.

The invention claimed is:

1. A method for inhibiting digestive lipase activity, the method comprising administering a digestive lipase activity inhibitor to a subject in need thereof, wherein the digestive lipase activity inhibitor comprises, as an active ingredient, linoleic acid.

2. The method according to claim 1, further comprising inhibiting an increase in blood triglyceride concentration by inhibiting digestive lipase activity.

3. The method according to claim 2, further comprising inhibiting fat absorption by inhibiting digestive lipase activity and inhibiting an increase in blood triglyceride concentration.

4. The method according to claim 1, wherein the digestive lipase activity inhibitor is administered in the form of a food composition or a pharmaceutical product.

5. The method according to claim 1, wherein the digestive lipase activity inhibitor comprises both the linoleic acid and oleic acid as active ingredients.

6. The method according to claim 1, wherein the digestive lipase is at least one lipase selected from the group consisting of a gastric lipase, an intestinal lipase, and a pancreatic lipase.

7. The method according to claim 1, wherein the digestive lipase activity inhibitor comprises the active ingredient in an amount 1% by mass or more and 5% by mass or less based on total amount of the digestive lipase activity inhibitor.

8. The method according to claim 1, wherein the digestive lipase activity inhibitor further comprises at least one material selected from the group consisting of amino acids, proteins, carbohydrates, fats and oils, sweeteners, minerals, vitamins, flavoring agents, excipients, and binders, lubricants, disintegrators, emulsifiers, surfactants, bases, solubilizers, and suspending agents.

9. The method according to claim 1, wherein the digestive lipase activity inhibitor is in shape of solid, liquid, or paste.

10. The method according to claim 1, wherein the subject is human.

11. The method according to claim 1, wherein the digestive lipase activity inhibitor is administered orally.

12. The method according to claim 1, wherein the digestive lipase activity inhibitor is administered in an amount 50 μg or more and 300 mg or less per dose.

* * * * *